United States Patent
Rathjen (10) Patent No.: US 11,090,191 B2
(45) Date of Patent: Aug. 17, 2021

(54) OPHTHALMOLOGICAL DEVICE FOR PROCESSING EYE TISSUE BY MEANS OF A PULSED PROCESSING LASER BEAM

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 187 days.

(21) Appl. No.: 16/132,911

(22) Filed: Sep. 17, 2018

(65) Prior Publication Data

US 2019/0083308 A1     Mar. 21, 2019

(30) Foreign Application Priority Data

Sep. 20, 2017   (EP) ..................................... 17020431

(51) Int. Cl.
*A61F 9/008*     (2006.01)
*A61B 18/20*    (2006.01)

(52) U.S. Cl.
CPC ........ *A61F 9/0084* (2013.01); *A61F 9/00827* (2013.01); *A61F 9/00836* (2013.01);
(Continued)

(58) Field of Classification Search
CPC .............. A61F 9/00736; A61F 9/00838; A61F 9/00831; A61F 9/00754; A61F 9/009;
(Continued)

(56) References Cited

U.S. PATENT DOCUMENTS 5,480,396 A * 1/1996 Simon ..................... A61F 9/008
                                                              606/4
6,210,401 B1 * 4/2001 Lai ......................... H01S 3/235
                                                              606/12
(Continued)

FOREIGN PATENT DOCUMENTS

DE    102008051644 A1    4/2010
EP        2596775 A1     5/2013
(Continued)

OTHER PUBLICATIONS

Feb. 28, 2018—U.S. Extended Search Report—App 17020431.7.

*Primary Examiner* — Erin M Piateski
(74) *Attorney, Agent, or Firm* — Banner & Witcoff, Ltd.

(57) ABSTRACT

An ophthalmological device for processing eye tissue comprises a laser source for generating a pulsed laser beam, a focusing optical unit for focusing a processing laser beam into the eye tissue, and a scanner system for deflecting the processing laser beam into the eye tissue. The ophthalmological device additionally comprises a beam splitting system disposed upstream of the scanner system and configured to generate the processing laser beam from the pulsed laser beam in such a way that the processing laser beam comprises two beam parts, wherein one of the beam parts is focused by the focusing optical unit onto the lower outer surface of a lenticule to be cut in the eye tissue, and the other beam part is focused onto the upper outer surface of the lenticule to be cut, such that both the lower and the upper outer surfaces are processed when the processing laser beam is deflected into the eye tissue.

20 Claims, 8 Drawing Sheets

(52) U.S. Cl.
CPC ....... *A61B 18/20* (2013.01); *A61F 2009/0087* (2013.01); *A61F 2009/00872* (2013.01); *A61F 2009/00897* (2013.01)

(58) Field of Classification Search
CPC .............. A61F 9/00812; A61F 9/00825; A61F 9/00814; A61F 9/00834; A61F 9/008; A61F 9/0084; A61F 2/1602; A61F 9/00836; A61F 2009/00887; A61F 2009/00895; A61F 2009/00865; A61F 2009/00897; A61F 2009/00878; A61F 2009/0087; A61F 2009/00882; A61F 2009/00844; A61F 2009/00851; A61F 2009/00889; A61B 18/20; A61B 90/361; A61B 2018/00577
USPC ........................................................... 606/4
See application file for complete search history.

(56) References Cited

U.S. PATENT DOCUMENTS

| | | | | |
|---|---|---|---|---|
| 2001/0037105 | A1* | 11/2001 | Lin | A61F 9/008 606/5 |
| 2006/0195076 | A1* | 8/2006 | Blumenkranz | A61F 9/00736 606/4 |
| 2011/0237999 | A1* | 9/2011 | Muller | A61B 3/107 604/20 |
| 2013/0310816 | A1* | 11/2013 | Rathjen | A61F 9/008 606/4 |
| 2016/0051405 | A1* | 2/2016 | Hertzberg | A61F 9/00804 606/4 |

FOREIGN PATENT DOCUMENTS

| | | |
|---|---|---|
| EP | 2990015 A1 | 3/2016 |
| WO | 2006074469 A2 | 7/2006 |
| WO | 2016049442 A1 | 3/2016 |

* cited by examiner

OPHTHALMOLOGICAL DEVICE FOR PROCESSING EYE TISSUE BY MEANS OF A PULSED PROCESSING LASER BEAM

TECHNICAL FIELD

The present invention relates to an ophthalmological device for processing eye tissue by means of a processing laser beam that is directed into the eye tissue in a focused manner by a scanner system.

PRIOR ART

For processing eye tissue by means of a laser beam, a processing region is scanned with laser pulses by means of the pulsed laser beam being deflected in one or two scanning directions by means of suitable scanner systems (deflection devices). The deflection of the light beams or of the laser pulses, for example femtosecond laser pulses, is generally performed by means of movable mirrors which are pivotable about one or two scanning axes, for example by means of galvano scanners, piezo scanners, polygon scanners or resonance scanners.

U.S. Pat. No. 7,621,637 describes a device for processing eye tissue, said device having a base station with a laser source for generating laser pulses and a scanner arranged in the base station with movable deflection mirrors for deflecting the laser pulses in a scanning direction. The deflected laser pulses are transmitted via an optical transmission system from the base station to an application head, which moves over a working region in accordance with a scanning pattern by means of a mechanically moved projection optical unit. The deflection in the scanning direction, which is much faster compared with the mechanical movement, is superimposed in the application head onto the mechanical movement of the projection optical unit and thus onto the scanning pattern thereof. A fast scanner system in the base station enables a fine movement of the laser pulses (microscan), which is superimposed onto the scanning pattern of the movable projection optical unit that covers a large processing region, for example the entire eye.

Although known systems of this type make it possible to process simple scanning patterns, for example to cut a tissue flap, this generally being performed as a large area segment with a simple edge geometry, in the case of applications which involve not only making tissue cuts in a substantially horizontally oriented processing area on a common focal area, but also intending to make cuts with a vertical cut component over different focus heights, e.g. cuts that are vertical or run obliquely with respect to the horizontal, in order to cut lenticules in the eye tissue, for example, the vertical movement of the projection optical unit or of a zoom system for a vertical variation of the focus and thus of the cut height proves to be too slow for making cuts with a vertical component, that is to say with a variable depth of focus during cutting, at a speed comparable with cutting speeds in the horizontal processing area.

US 2016/0089270 describes a system and method for cutting lenticules in eye tissue. In accordance with US 2016/0089270, for this purpose rectilinear fast scanning lines are superimposed on slower processing lines which are moved along meridians of the lenticule. The rectilinearity of the fast scanning lines gives rise to cuts which deviate in the shape thereof from the desired surface curvature of the lenticule and therefore cause aberrations. Moreover, moving the processing lines along the meridians in each case over the distance of a lenticule width necessitates a vertical focus displacement of the order of magnitude and to the extent of the thickness of the lenticule to be cut, which is associated firstly with corresponding complexity and costs for displaceable optical units and movable lenses configured for that purpose, and secondly with attendant losses in processing speed. Furthermore, the fast scanning lines, on account of their fixed horizontal orientation, do not allow the best possible adaptation of cuts to lenticule surfaces, particularly not if they deviate from a spherical shape. In addition, it should be taken into consideration that when cutting lenticule surfaces at different depth positions it is necessary to take precautions in order firstly to prevent deeper positions from being shaded by more highly positioned cuts, but secondly not to impair the precision and accuracy of the cuts and if possible not to lengthen the processing time unnecessarily.

These known systems involve sequentially cutting firstly a lower surface of a lenticule and then an upper surface of the lenticule. If the eye tissue moves between these two steps or the focus guidance does not follow accurately predefined cutting coordinates, then this results in a deviation in the thickness of the lenticule, which leads to refractive aberrations.

SUMMARY OF THE INVENTION

It is an object of the present invention to propose an ophthalmological device for processing eye tissue by means of a processing laser beam which does not have at least some disadvantages of the known systems. In particular, it is an object of the present invention to propose an ophthalmological device for processing eye tissue by means of a processing laser beam which enables efficient cutting of lenticules in eye tissue.

According to the present invention, these aims are achieved by means of the features of the independent claims. Further advantageous embodiments are additionally evident from the dependent claims and the description.

An ophthalmological device for processing eye tissue comprises a laser source configured to generate a pulsed laser beam, a focusing optical unit configured to focus a processing laser beam into the eye tissue, and a scanner system configured to direct the processing laser beam into the eye tissue in accordance with predefined scanning patterns.

The aims mentioned above are achieved by the present invention in particular by virtue of the fact that the ophthalmological device additionally comprises a beam splitting system disposed upstream of the scanner system and configured to generate the processing laser beam from the pulsed laser beam in such a way that the processing laser beam comprises a first beam part and a second beam part, wherein the first beam part is focused by the focusing optical unit onto a first outer surface of a lenticule to be cut in the eye tissue, and the second beam part is focused onto a different, second outer surface of the lenticule to be cut in the eye tissue, and that, in the course of directing the processing laser beam into the eye tissue by means of the scanner system, the first outer surface is processed by the first beam part and the second outer surface is processed by the second beam part. The generation of the processing laser beam comprising two beam parts, which, without adjustment of the focusing optical unit, are focused both onto the more deeply located lower outer surface of the lenticule to be cut and onto the comparatively more highly located upper outer surface of the lenticule, enables the lenticule to be cut more efficiently and more rapidly, since the lower and upper outer surfaces of the lenticule can be processed simultaneously with each setting of the focusing optical unit and the scanner system. Moreover, simultaneously cutting the lower and upper outer surfaces of the lenticule reduces undesired deviations from the desired thickness of the lenticule which may arise on account of movements of the tissue during the cutting process.

In one embodiment variant, the beam splitting system comprises a divergence modulator disposed upstream of the scanner system and configured to modulate a divergence of the first beam part or of the second beam part, such that the first beam part and the second beam part have a different divergence, in such a way that the first beam part is focused onto the first outer surface by the focusing optical unit and the second beam part is focused onto the second outer surface. The divergence modulator disposed upstream of the scanner system and the divergence modulation of at least one of the beam parts that is effected thereby make it possible to generate a processing laser beam with a dual focus for processing two outer surfaces of a lenticule at different depth positions, without the focusing optical unit or the scanner system having to be set differently for this purpose. In other words, the setting of the focusing optical unit and of the scanner system for processing a working point in the eye tissue brings about the processing at two different processing points in the eye tissue, one on the lower outer surface of the lenticule and one on the upper outer surface of the lenticule.

In one embodiment variant, the beam splitting system comprises a first divergence modulator configured to generate the first beam part with a first divergence, and a second divergence modulator configured to generate the second beam part with a second divergence, which is different from the first divergence.

In one embodiment variant, the focusing optical unit is configured to focus the processing laser beam in the eye tissue onto a set cutting position. The first divergence modulator is configured to generate the first beam part with the first divergence in such a way that the first beam part is focused in the eye tissue relative to the set cutting position onto the first outer surface by the focusing optical unit, and the second divergence modulator is configured to generate the second beam part with the second divergence in such a way that the second beam part is focused in the eye tissue relative to the set cutting position onto the second outer surface by the focusing optical unit.

In one embodiment variant, the beam splitting system comprises a beam splitter which is configured to split the pulsed laser beam into a first beam bundle and into a second beam bundle.

In one embodiment variant, the beam splitter is configured to feed a first pulse of the pulsed laser beam to the first beam bundle, and to feed a second pulse of the pulsed laser beam, said second pulse directly succeeding the first pulse, to the second beam bundle.

In one embodiment variant, the beam splitter comprises an optical modulator, which is coupled to the laser source in a synchronized manner and is configured to feed the first pulse of the pulsed laser beam to the first beam bundle, and to feed the second pulse of the pulsed laser beam to the second beam bundle.

In one embodiment variant, the beam splitter comprises an optical beam splitter configured to split the pulsed laser beam into the first beam bundle and into the second beam bundle. The beam splitter comprises a first optical modulator, which is arranged in the first beam bundle in a manner coupled to the laser source in a synchronized manner and is configured to mask out the second pulse of the pulsed laser beam in the first beam bundle. The beam splitter comprises a second optical modulator, which is arranged in the second beam bundle in a manner coupled to the laser source in a synchronized manner and is configured to mask out the first pulse of the pulsed laser beam in the second beam bundle.

In one embodiment variant, the beam splitting system comprises a beam combiner configured to combine the first beam bundle and the second beam bundle to form the processing laser beam.

In one embodiment variant, the beam combiner is configured to combine the first beam bundle and the second beam bundle to form the processing laser beam with an angle between a beam axis of the first beam bundle and a beam axis of the second beam bundle. The processing laser beam thus comprises two superimposed beam bundles having differently oriented beam axes. In the case of a combination with the embodiment variant in which the successive laser pulses are alternately allocated to the first beam bundle and to the second beam bundle, the processing laser beam has successive laser pulses which each have a pulse direction or more precisely projection axis or beam axis that is different by the relevant angle.

In one embodiment variant, the beam splitting system comprises a beam cross section splitter configured to feed a first cross-sectional region of the pulsed laser beam to the first beam part, and to feed a second cross-sectional region of the pulsed laser beam to the second beam part, wherein the first cross sectional region and the second cross-sectional region do not overlap.

In one embodiment variant, the beam splitting system comprises a beam cross section combiner configured to feed the first cross-sectional region of the pulsed laser beam to a first cross-sectional region of the processing laser beam, and to feed the second cross-sectional region of the pulsed laser beam to a second cross-sectional region of the processing laser beam, wherein the first cross-sectional region of the processing laser beam and the second cross-sectional region of the processing laser beam do not overlap.

In one embodiment variant, the scanner system is configured to direct the processing laser beam into the eye tissue in accordance with a predefined cutting line scanning pattern, wherein the first beam part generates a first cutting line on the first outer surface of the lenticule and the second beam part generates a second cutting line on the second outer surface of the lenticule.

In one embodiment variant, the scanner system comprises a first scanner module configured to guide the processing laser beam in accordance with a first component of the predefined cutting line scanning pattern in an advance direction along a processing line, and a second scanner module configured to direct the processing laser beam in accordance with a second component of the predefined cutting line scanning pattern, said second component being superimposed on the first component, along a scanning line running transversely with respect to the processing line, at a significantly higher scanning speed in comparison with the scanning speed of the first scanner module in the advance direction, wherein the first beam part generates a first cutting line having the first component and the superimposed second component on the first outer surface of the lenticule and the second beam part generates a second cutting line having the first component and the superimposed second component on the second outer surface of the lenticule.

In one embodiment variant, the beam splitting system is configured to generate the first beam part and the second beam part in such a way that the first beam part is focused by the focusing optical unit onto the first outer surface, which is further away from the focusing optical unit than the second outer surface, onto which the second beam part is focused by the focusing optical unit.

In one embodiment variant, the ophthalmological device comprises an intensity modulator configured to modulate the light intensity of the first beam part in relation to the light intensity of the second beam part.

BRIEF DESCRIPTION OF THE DRAWINGS

One embodiment of the present invention is described below on the basis of an example. The example of the embodiment is illustrated by the following attached figures.

WAYS OF EMBODYING THE INVENTION

In FIGS. 1-8, the reference sign 1 refers in each case to an ophthalmological device for processing eye tissue 20 by means of laser pulses. An eye 2 is schematically illustrated in cross section in FIG. 1. In this case, the reference sign 20 refers to eye tissue to be processed, in particular the cornea. As is illustrated schematically in FIGS. 1-8, the ophthalmological device 1 is configured to cut a lenticule 21 in the eye tissue 20, in particular in the cornea, said lenticule 21 having an upper outer surface 21o and a lower outer surface 21u. The upper outer surface 21o faces the external surface of the cornea 20 and the ophthalmological device 1, respectively. The lower outer surface 21u faces away from the external surface of the cornea 20 and the ophthalmological device 1, respectively.

As is illustrated schematically in FIGS. 1-8, the ophthalmological device 1 comprises a laser source 11. The laser source 11 is configured to generate a pulsed laser beam P. In one embodiment variant, the laser source 11 is configured to generate a laser beam P comprising femtosecond laser pulses.

The ophthalmological device 1 additionally comprises a beam splitting system 12 configured to generate from the pulsed laser beam P a processing laser beam L comprising two beam parts L1, L2, as will be described below.

The ophthalmological device 1 additionally comprises a scanner system 13, with the beam splitting system 12 being disposed upstream thereof, and a focusing optical unit 14. The processing laser beam L generated by the beam splitting system 12 is fed to the scanner system 13 for the purpose of processing the eye tissue 20. The scanner system 13 is configured to direct the processing laser beam L into the eye tissue 20 in accordance with a predefined x/y-scanning pattern via the focusing optical unit 14 in order to make cuts in the eye tissue 20. In one embodiment variant, the scanner system 13 comprises as scanner module a drive system, which is coupled to the focusing optical unit 14 and is configured to move the focusing optical unit 14 in x/y processing directions of a processing plane arranged perpendicularly to an optical axis y of the focussing optical unit 14. In one embodiment variant, the scanner system 13 comprises, as an alternative or in addition to the drive system, one or more beam deflecting x/y-scanner modules, e.g. scanner modules having movable mirrors which are pivotable about one or two scanning axes, for example galvano, piezo, polygon or resonance scanner modules, or AOM (acusto-optical modulator) or EOM (electro-optical modulator) scanner module. In one embodiment variant, one scanner module of the scanner systems 13 is configured as a slow scanner to guide the processing laser beam L in accordance with a first component of the predefined cutting line scanning pattern in an advance direction along a processing line, and a further scanner module of the scanner system is 13 is configured as a fast scanner to direct the processing laser beam L in accordance with a second component of the predefined cutting line scanning pattern, said second component being superimposed on the first component, along a scanning line extending transversely with respect to the processing line, at a comparatively significantly higher scanning speed in comparison with the scanning speed of the slow scanner in the advance direction.

The focusing optical unit 14 is configured to focus the processing laser beam L into the eye tissue 20. The focusing optical unit 14 comprises one or more optical lenses. For setting the focal length (focus), the focusing optical unit 14 comprises at least one movable lens. Alternatively, the entire focusing optical unit 14 can be displaced. In one embodiment variant, the focusing optical unit 14 additionally comprises one or more drives, e.g. electric motors, for the automated movement of the movable lens(es) or respectively of the entire focusing optical unit 14 and the attendant setting and adaptation of the focus or respectively of the focal surface(s) that can be scanned and processed by the scanner system 13.

As is illustrated schematically in FIGS. 1-8, the ophthalmological device 1 comprises a circuit 10 for controlling the laser source 11, the scanner system 13, and the focusing optical unit 14, and also below-described divergence modulators 121, 122, beam splitters 124, beam combiner 125 and intensity modulator(s). The circuit 10 realizes a programmable control device and comprises for example one or more processors with program and data memory and also programmed software modules for controlling the processors, and/or other programmable circuits or logic units such as ASICs (Application Specific Integrated Circuit). For controlling the various components and modules of the ophthalmological device 1, the circuit 10 generates corresponding control signals for these components and modules.

In one variant, the ophthalmological device 1 comprises an intensity modulator (in addition to the already existing intensity modulator of the laser source 11) configured to modulate the light intensity of the first beam part L1 in relation to the light intensity of the second beam part L2. In one embodiment variant, the intensity modulator is implemented by virtue of the circuit 10 controlling and modulating the intensity or power of the laser source 11 in a manner synchronized with the generation of the beam parts L1, L2. In one embodiment variant implemented in the beam path of one of the beam parts L1, L2, the intensity modulator comprises a polarization rotator (e.g. lambda/2 plates) and/or polarization beam splitter. In one embodiment variant, the intensity modulator is implemented in the beam combiner 125, wherein polarization-sensitive coatings perform the task of intensity modulation by virtue of only a specific intensity portion of the radiation being coupled in at the common beam axis.

As mentioned above, the beam splitting system 12 is configured to generate from the pulsed laser beam P a processing laser beam L comprising two beam parts L1, L2. As is illustrated in FIGS. 1-7, the beam parts L1 and L2 have a different divergence, such that they are focused at different focal depths or focal lengths by the focussing optical unit 14, without an adjustment of the focussing optical unit 14 being carried out or having to be carried out in the process. In the embodiment variants in accordance with FIGS. 2, 4 and 5, the beam parts L1 and L2 are different, non-overlapping (spatially separated) beam cross sections W10, W20 of the processing laser beam L. In the embodiment variants in accordance with FIGS. 3, 6-8, 10 and 11, the beam parts L1 and L2 of the processing laser beam L are generated from two different beam bundles L1*, L2*. In the embodiment variant in accordance with FIG. 6, the laser pulses of the beam parts L1 and L2 are temporally shifted with respect to one another in such a way that in the processing laser beam L alternately in each case a laser pulse from one of the two beam parts L1, which is generated by one of the beam bundles L1*, succeeds the next laser pulse of the other of the beam parts L2, which is generated by the other beam bundle L2*, as is described below and illustrated schematically in FIG. 10a. In the embodiment variants in accordance with FIGS. 3, 7, 8, 10 and 11, the beam parts L1 and L2 of the processing laser beam L are generated from two different beam bundles L1*, L2*, which are generated from the pulsed laser beam P by beam splitting, wherein, depending on the variant, the beam energy of the pulsed laser beam P is split between the beam bundles L1*, L2* or, as in accordance with the embodiment variant in FIG. 6, the laser pulses of the pulsed laser beam P are alternately switched to the two beam bundles L1*, L2*. In the embodiment variant in FIG. 4, the beam splitting system 12 comprises a beam cross section splitter 120 configured to separate a first cross-sectional region W1 of the pulsed laser beam P and a second cross-sectional region W2 of the pulsed laser beam P, which do not overlap. FIG. 12 illustrates two examples of non-overlapping beam cross sections W1, W2 of the pulsed laser beam P (in the upper part); on the left beam cross sections W1, W2 arranged concentrically; on the right beam cross sections W1, W2 arranged alongside one another, wherein the corresponding recombined, non-overlapping beam cross sections W10, W20 are illustrated in each case in the lower part of FIG. 12. In other variants, a segmented splitting of the beam cross section is provided, e.g. in the form of squares or sextants. The beam cross section splitter 120 is e.g. a reflection beam splitter that splits the beam cross section of the pulsed laser beam P. The beam cross section splitter 120 comprises e.g. a beam splitter cube which, by means of reflective coatings and/or masks, deflects or transmits the first cross-sectional region W1 and the second cross-sectional region W2 of the pulsed laser beam P in different directions. As is illustrated schematically in FIG. 4, the beam splitting system 12 additionally comprises at least one divergence modulator 121, 122 configured to dynamically vary the divergence of the laser beam part fed to it. In one variant having one divergence modulator 122, the beam cross section splitter 120 guides the corresponding cross-sectional region W2 of the pulsed laser beam P via the divergence modulator 122 to a beam combiner or a beam cross section combiner 123 of the beam splitting system 12, whereas the cross-sectional region W1 of the pulsed laser beam P is fed without divergence modulation directly to the beam combiner or beam cross section combiner 123. In one variant having two divergence modulators 121, 122, the beam cross section splitter 120 guides the cross-sectional regions W1 and W2 of the pulsed laser beam P via the respectively assigned divergence modulator 121, 122 to the beam combiner or beam cross section combiner 123 of the beam splitting system 12. The beam cross section combiner 123 comprises e.g. a beam splitter cube that is provided with reflective coatings and/or masks and is configured to feed the cross-sectional regions W1 and W2 of the pulsed laser beam P, said cross-sectional regions being fed directly from the beam cross section splitter 120 or via the divergence modulator 121, 122, to a first cross-sectional region W10 and a second cross-sectional region W20 of the processing laser beam L, wherein the two cross-sectional regions W10, W20 of the processing laser beam L do not overlap. As a result of the beam cross section splitting and the beam recombination or beam cross section recombination of the two differently divergence-modulated beam paths, shading and attendant influencing of the two generated foci of the beam parts L1, L2 are avoided. A combination of beam cross section splitter and beam cross section combiner is not absolutely necessary. One of the two elements can be replaced by a normal beam splitter if it is ensured that the other element brings about a separation of the cross-sectional regions W10 and W20 sufficiently accurately.

Figure 9:
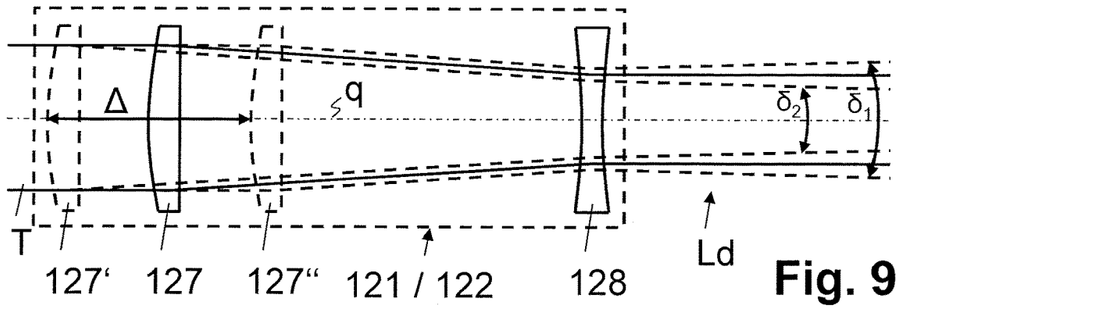
FIG. 9: shows a schematic cross section of a portion of the beam path in a divergence modulator with at least one displaceable lens and illustrates the divergence of the laser beam that is altered by the displacement of the lens.

FIG. 9 schematically illustrates one embodiment variant of the divergence modulator 121, 22 having two optical lenses 127, 128 arranged serially, at least one of which optical lenses is displaceable on an optical transmission axis q for the purpose of modulating the divergence of the laser beam part T fed. For the purpose of dynamically modulating the divergence of the laser beam part T fed, the movable lens 127 is coupled to a movement driver. As is evident in the example in FIG. 9, the laser beam part T fed has a corresponding divergence $\delta_2$ in the case of a first basic position 127' of the movable lens. In the case of a displacement of the movable lens 127 on the transmission axis w, the divergence of the laser beam part T fed varies continuously and has an altered divergence $\delta_1$ in the case of the position 127" displaced by the deflection distance Δ.

The processing laser beam L having the two cross-sectional regions W10, W20 that is generated from the pulsed laser beam P by the beam splitting system 12 is fed to the scanner system 13 for the purpose of cutting the upper and lower outer surfaces 21u, 210 of the lenticule 21 in the eye tissue 20.

In the case of the variant having one divergence modulator 122, the circuit 10 controls the focusing optical unit 14 in a synchronized manner with the scanner system 13 such that the beam part L1 of the processing laser beam L, which beam part is formed by the non-divergence-modulated cross-sectional region W1 or respectively W10, is focused onto the lower outer surface 21u of the lenticule 21 to be cut. At the same time and in a synchronized manner, the circuit 10 controls the divergence modulator 122 such that the beam part L2 of the processing laser beam L, which beam part is formed by the divergence-modulated cross-sectional region W2 or respectively W20, with the setting of the focusing optical unit 14 remaining the same, is focused onto the upper outer surface 210 of the lenticule 21 to be cut.

In the case of the variant having two divergence modulators 121, 122, the circuit 10 controls the focusing optical unit 14 such that a fixed cutting position or cutting depth is set (after setting has been carried out, the focusing optical unit 14 can remain fixed and need not be displaced further). The circuit 10 controls the divergence modulator 121 in a synchronized manner with the scanner system 13 such that the beam part L1 of the processing laser beam L, which beam part is formed by the divergence-modulated cross-sectional region W1 or respectively W10, with the setting of the focusing optical unit 14 remaining fixed, is focused onto the lower outer surface 21u of the lenticule 21 to be cut. At the same time and in a synchronized manner, the circuit 10 controls the divergence modulator 122 such that the beam part L2 of the processing laser beam L, which beam part is formed by the divergence-modulated cross-sectional region W2 or respectively W20, with the setting of the focusing optical unit 14 remaining fixed, is focused onto the upper outer surface 210 of the lenticule 21 to be cut.

The scanner system 13 directs the processing laser beam L with regard to the x/y positioning for processing the eye tissue 20. For each x/y processing point determined by the scanner system 13 in accordance with a defined scanning pattern, the circuit 10 controls the divergence modulation of the divergence modulators 121, 122, such that a focused processing of the eye tissue 20 on the lower outer surface 21u is effected by means of the beam part L1 and a focused processing of the eye tissue 20 on the upper outer surface 210 of the lenticule is effected by means of the beam part L2, without a change in the focusing or focusing optical unit 14 being or having to be carried out for this purpose. Depending on focusing range and/or technical implementation, a setting of the focusing optical unit can also be entirely dispensed with in the case of two divergence modulators.

Figure 1:
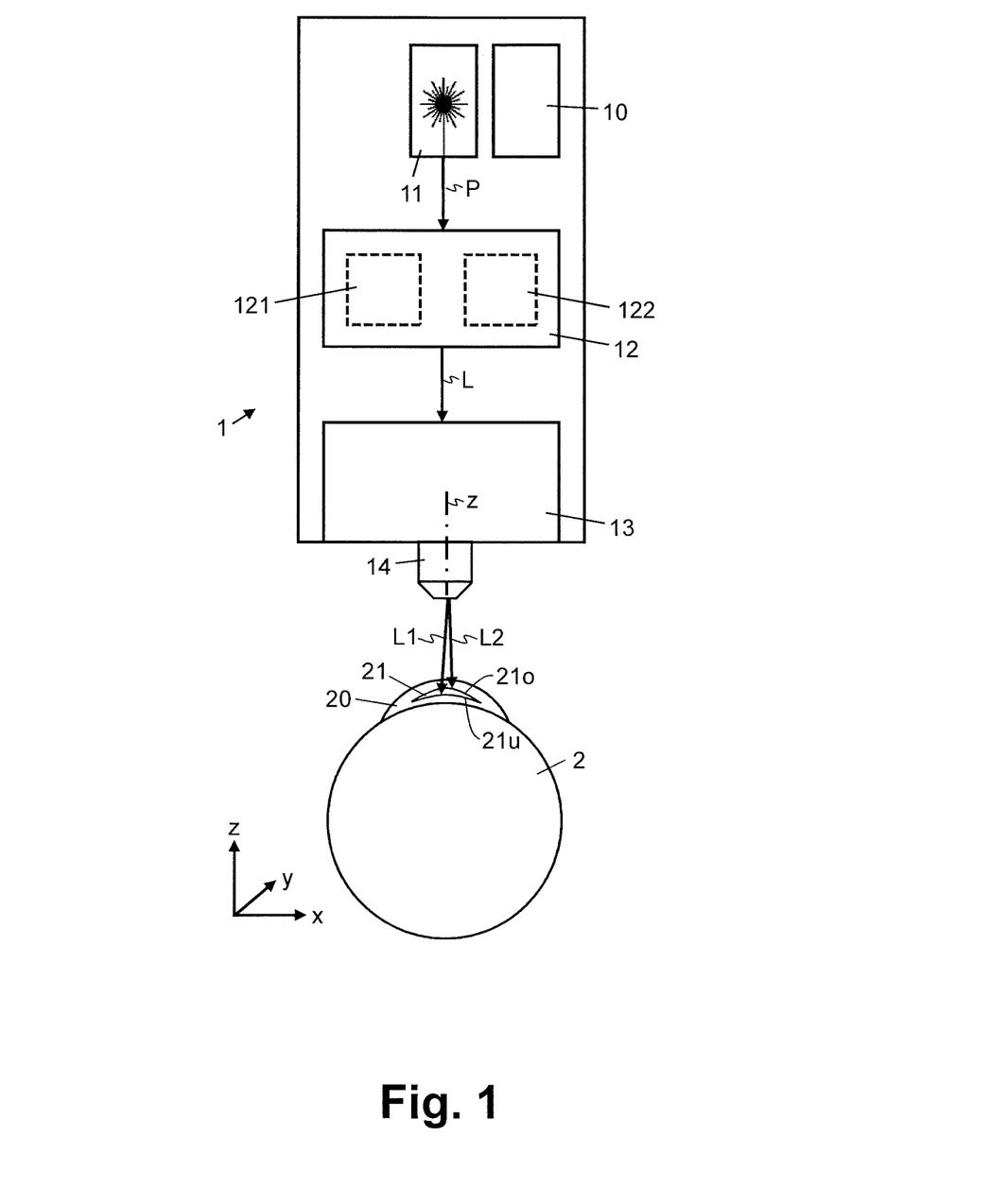
FIG. 1: shows a block diagram of an ophthalmological device for processing eye tissue by means of a pulsed laser beam, wherein a processing laser beams having two beam parts is generated, which are focused onto different outer surfaces of a lenticule to be cut in the eye tissue, as is illustrated schematically in cross section.
Figure 2:
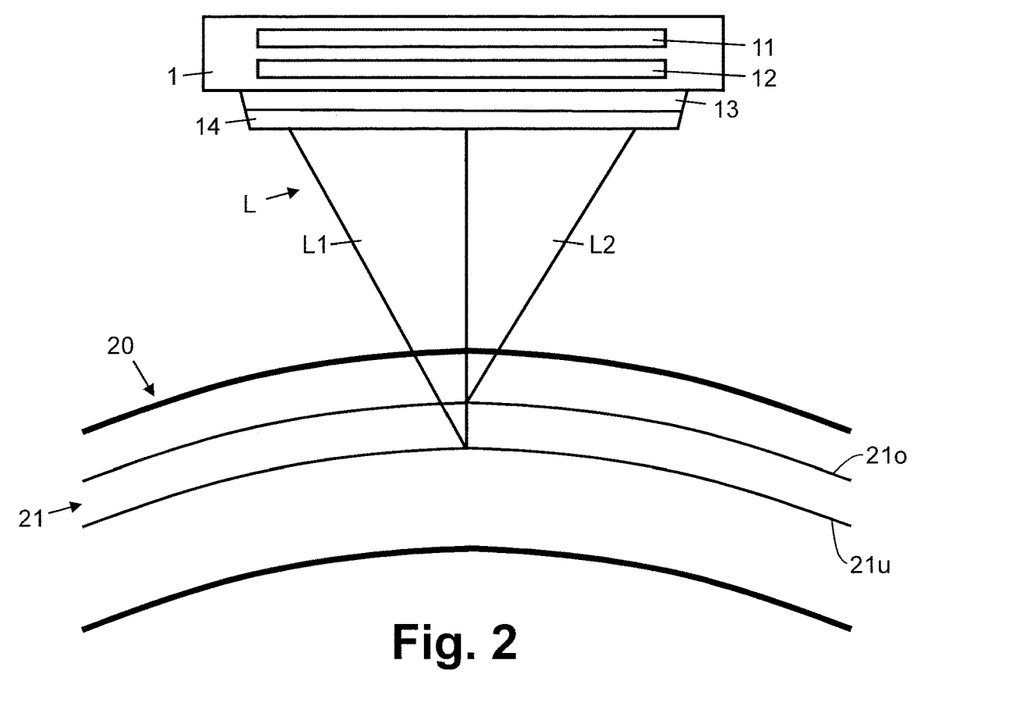
FIG. 2: schematically shows in cross section the processing laser beam of an ophthalmological device, which processing laser beam comprises two beam parts which are focused onto different outer surfaces of a lenticule to be cut in the eye tissue and which are formed by two non-overlapping cross-sectional regions of the processing laser beam.
Figure 3:
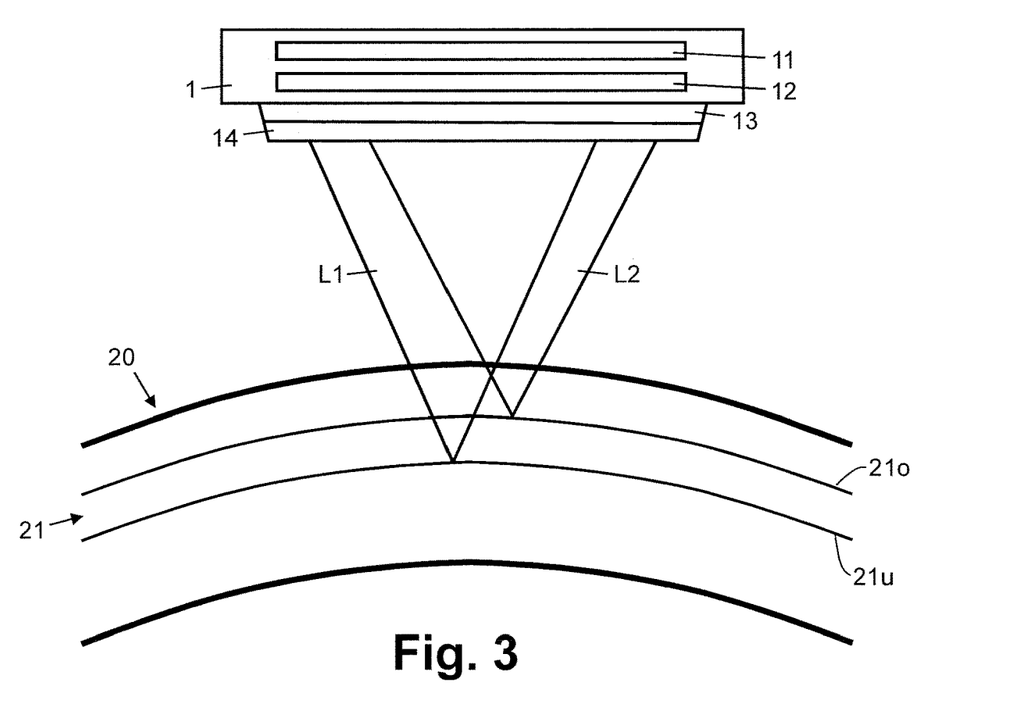
FIG. 3: schematically shows in cross section the processing laser beam of an ophthalmological device, which processing laser beam comprises two beam parts which are focused onto different outer surfaces of a lenticule to be cut in the eye tissue and which are formed by two beam bundles of the pulsed laser beam.
Figure 4:
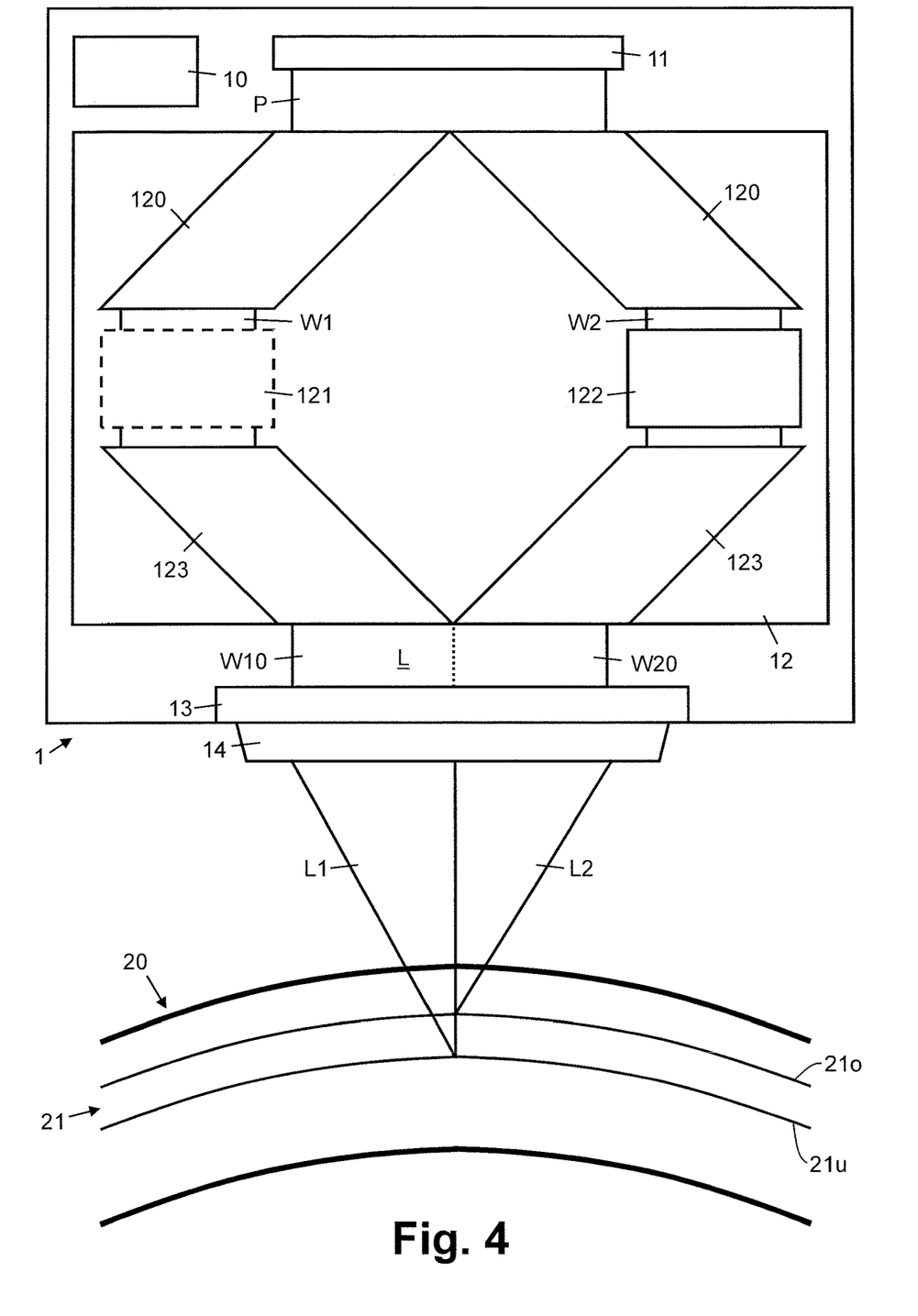
FIG. 4: shows a block diagram of an ophthalmological device for processing eye tissue by means of a pulsed laser beam, which ophthalmological device comprises a beam cross section splitter, a divergence modulator and a beam cross section combiner for generating a processing laser beam having two beam parts, which are formed by two non-overlapping cross-sectional regions of the processing laser beam and are focused onto different outer surfaces of a lenticule to be cut in the eye tissue, as is illustrated schematically in cross section.
Figure 5:
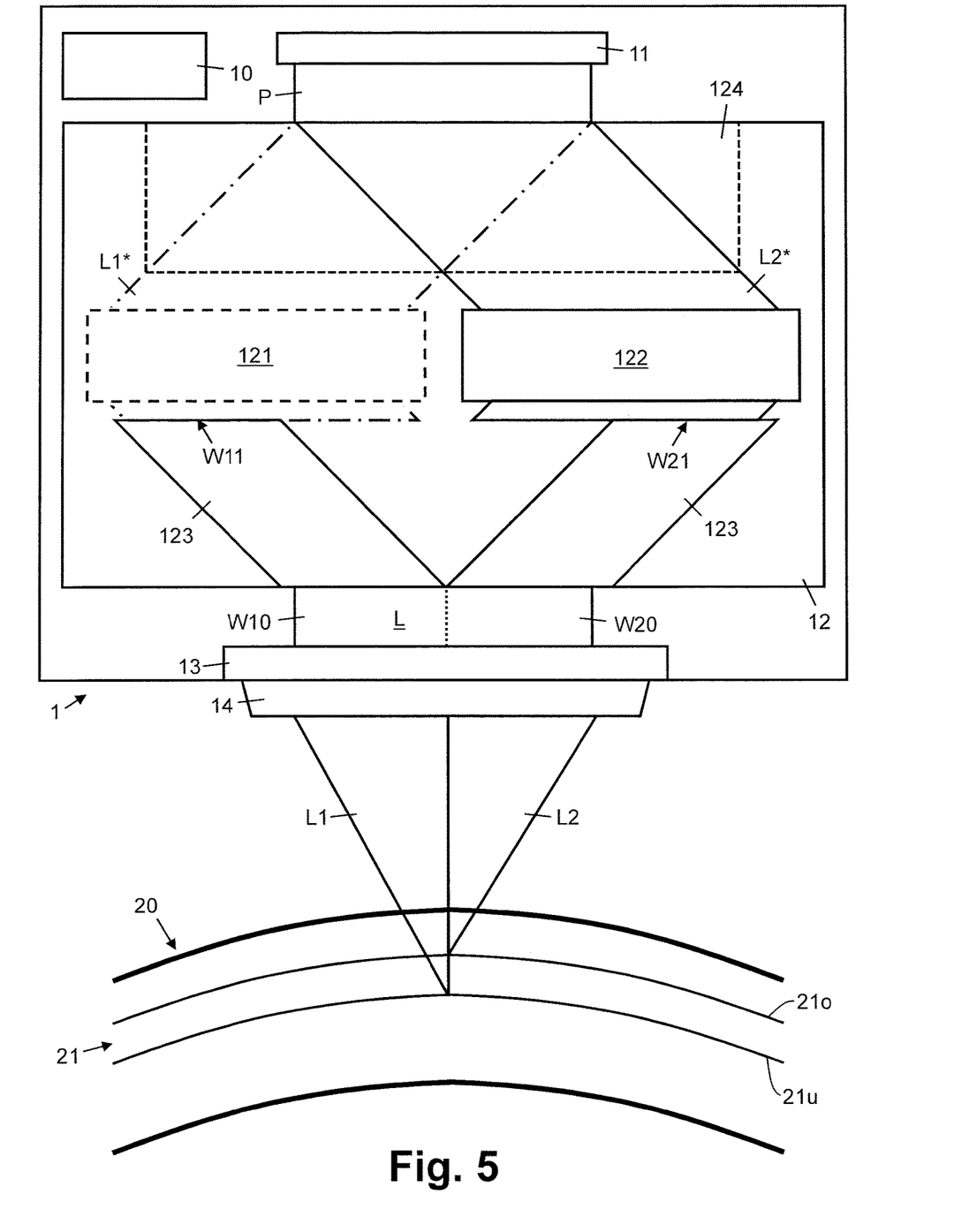
FIG. 5: shows a block diagram of an ophthalmological device for processing eye tissue by means of a pulsed laser beam, which ophthalmological device comprises a beam splitter, a divergence modulator and a beam cross section combiner for generating a processing laser beam having two beam parts, which are formed by two non-overlapping cross-sectional regions of the processing laser beam and are focused onto different outer surfaces of a lenticule to be cut in the eye tissue, as is illustrated schematically in cross section.

The embodiment variant in FIG. 5 differs from that in accordance with FIG. 4 by virtue of a differently configured beam splitting system 12 and a correspondingly adapted control by the circuit 10. The beam splitting system 12 in accordance with FIG. 5 comprises a beam splitter 124 configured to split the pulsed laser beam P into two beam bundles L1* and L2*. As in the embodiment variant in FIG. 4, the beam splitting system 12 comprises one or two divergence modulators 121, 122, via which the beam splitter 124 guides the beam bundles L1* and L2*. In the variant with one divergence modulator 122, the beam splitter 124 guides the corresponding beam bundle L2* of the pulsed laser beam P via the divergence modulator 122 to a beam combiner or beam cross section combiner 123 of the beam splitting system 12, whereas the beam bundle L1* of the pulsed laser beam P is fed without divergence modulation directly to the beam combiner or beam cross section combiner 123. In the case of the variant having two divergence modulators 121, 122, the beam splitter 124 guides the beam bundles L1* and L2* of the pulsed laser beam P via the respectively assigned divergence modulator 121, 122 to the beam combiner or beam cross section combiner 123 of the beam splitting system 12.

Figure 6:
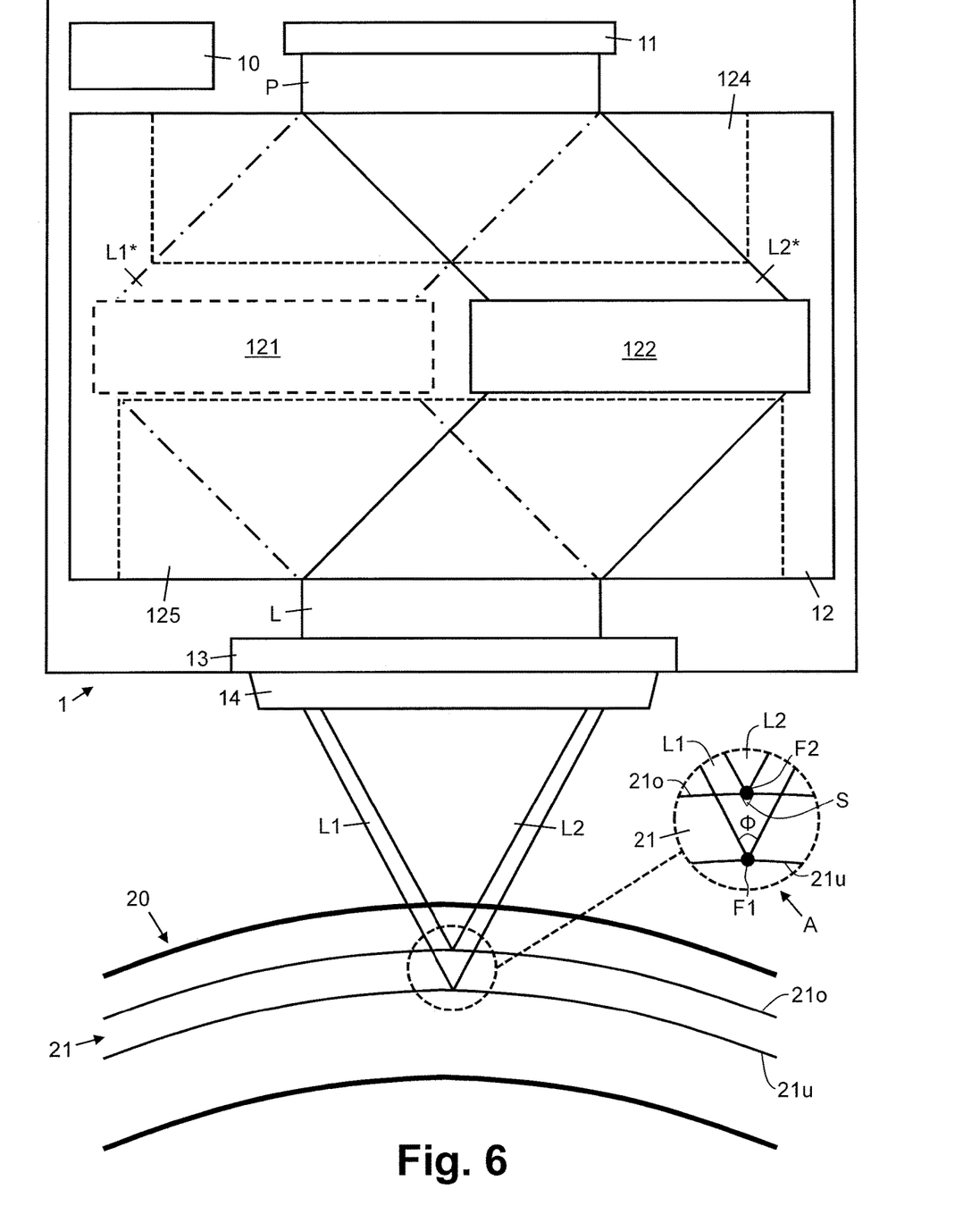
FIG. 6: shows a block diagram of an ophthalmological device for processing eye tissue by means of a pulsed laser beam, which ophthalmological device comprises a beam splitter, a divergence modulator and a beam combiner for generating a processing laser beam having two coaxially proceeding beam parts, which are formed by two beam bundles having alternately assigned laser pulses of the pulsed laser beam and are focused onto different outer surfaces of a lenticule to be cut in the eye tissue, as is illustrated schematically in cross section.

In the embodiment variant in FIG. 6 (optionally also in the embodiment variants in FIGS. 7 and 8), the beam splitter 124 is configured, for the purpose of splitting the pulsed laser beam P into two beam bundles L1*, L2*, to feed successive laser pulses of the pulsed laser beam P alternatively either to the first beam bundle L1* or to the second beam bundle L2*. The circuit 10 synchronizes the beam splitter 124 with the laser source 11 and the scanner system 13 in such a way that the order is effected such that, from the two successive laser pulses that are directed into the eye tissue 20 by the scanner system 13 without altered deflection of the processing beam L, the first laser pulse is allocated to the first beam bundle L1* or respectively beam part L1, which is focused onto the lower outer surface 21u, and that the directly succeeding second laser pulse is allocated to the second beam bundle L2* or respectively beam part L2, which is focused onto the upper outer surface 210. As a result of the alternating pulse sequence, a laser pulse focused firstly onto the lower outer surface 21u followed by a laser pulse focused onto the upper outer surface 210, shading and attendant influencing of the two generated foci of the beam parts L1, L2 can be avoided without different beam angles of the two beam parts L1, L2 being required for this purpose.

In one embodiment variant, the beam splitter 124 comprises an optical modulator embodied as a (fast) optical switch, e.g. AOM or EOM, which is coupled to the laser source 11 in a synchronized manner and is configured to feed the first pulse of the pulsed laser beam P to the first beam bundle L1* and to feed the second pulse of the pulsed laser beam P to the second beam bundle L2*.

In an alternative embodiment variant, the beam splitter 124 comprises an optical beam splitter configured to split the pulsed laser beam P into the first beam bundle L1* and into the second beam bundle L2*. The beam splitter 124 additionally comprises two optical modulators embodied as (fast) optical switches, e.g. AOM or EOM, which are arranged in the first beam bundle L1* and respectively in the second beam bundle L2* in a manner coupled to the laser source 11 in a synchronized manner. The first optical modulator is configured to mask out the second pulse of the pulsed laser beam P in the first beam bundle L1*. The second optical modulator is configured to mask out the first pulse of the pulsed laser beam P in the second beam bundle L2*.

In one embodiment variant, the optical modulators comprise EOM modules which are configured to modulate the polarization of the incident pulsed laser beam P and are combined with polarization-sensitive beam splitters and/or polarization filters in order to generate the split beam bundles L1* and L2*.

As is illustrated schematically by the shadow cone S in the enlarged excerpt A in FIG. 6, at the focus F2 of the beam part L2 focused onto the upper outer surface 210 of the lenticule 21, as a result of the interaction of an incident laser pulse with the eye tissue, shading of the underlying eye tissue is caused. This shading reduces the incident energy at the focus F1 of the beam part L1 on the lower outer surface 21u of the lenticule 21. In the case of short laser pulses, for example femtosecond laser pulses (fs), e.g. 100 fs, this impairment is relatively small and the pulse modulation described above can be dispensed with since, as a result of the short pulse duration of an individual laser pulse, disturbing (large) blisters are produced only after a time delay. Given large focus angles Φ, e.g. Φ>30°, and a certain minimum distance between the upper and lower outer surfaces 210, 21u of the lenticule 21, e.g. greater than 20 μm in the case of an interaction region of approximately 2 μm around the focus F2, that is to say an interaction region smaller than approximately 10% of the thickness of the lenticule 21, this reduction of the beam energy at the focus F1 on the lower outer surface 21u of the lenticule 21 is small and can be compensated for by a corresponding increase in the intensity of the beam part L1 or respectively the beam bundle L1*. To that end, the intensity modulator (or the circuit 10 for controlling the laser source is configured to correspondingly increase the light intensity of the first beam part L1 or respectively of the first beam bundle L1* (in relation to the light intensity of the second beam part L2 or respectively of the second beam bundle L2*) in order to compensate for the shading by the shadow cone S (or the resultant reduced beam energy on the lower outer surface 21u of the lenticule 21) that is caused by the interaction of laser pulses at the focus F2 on the upper outer surface 210 of the lenticule 21.

Figure 7:
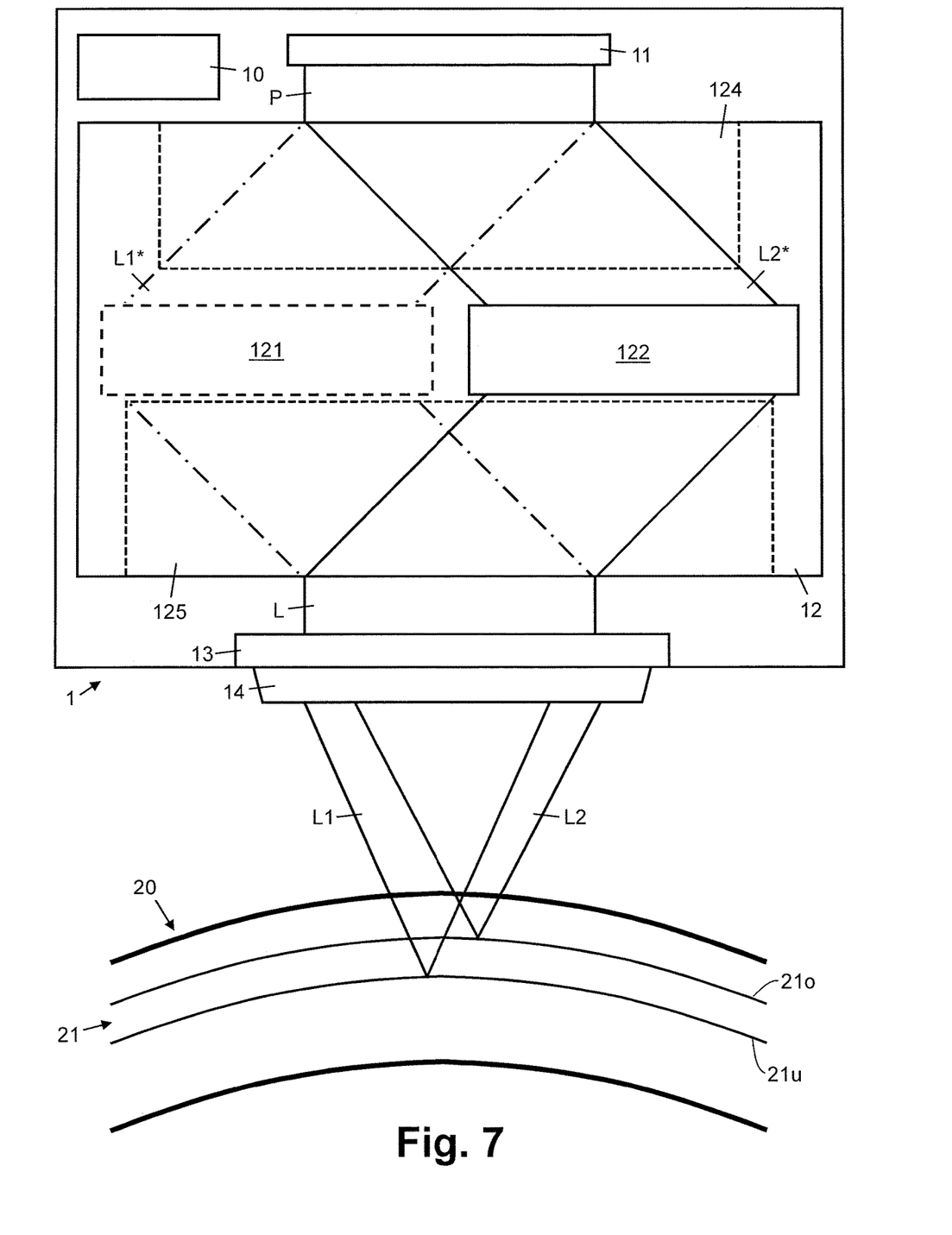
FIG. 7: shows a block diagram of an ophthalmological device for processing eye tissue by means of a pulsed laser beam, which ophthalmological device comprises a beam splitter and a beam combiner for generating a processing laser beam having two beam parts, which are formed by two beam bundles of the pulsed laser beam, said beam bundles proceeding at an angle with respect to one another, and are focused onto different outer surfaces of a lenticule to be cut in the eye tissue, as is illustrated schematically in cross section.
Figure 8:
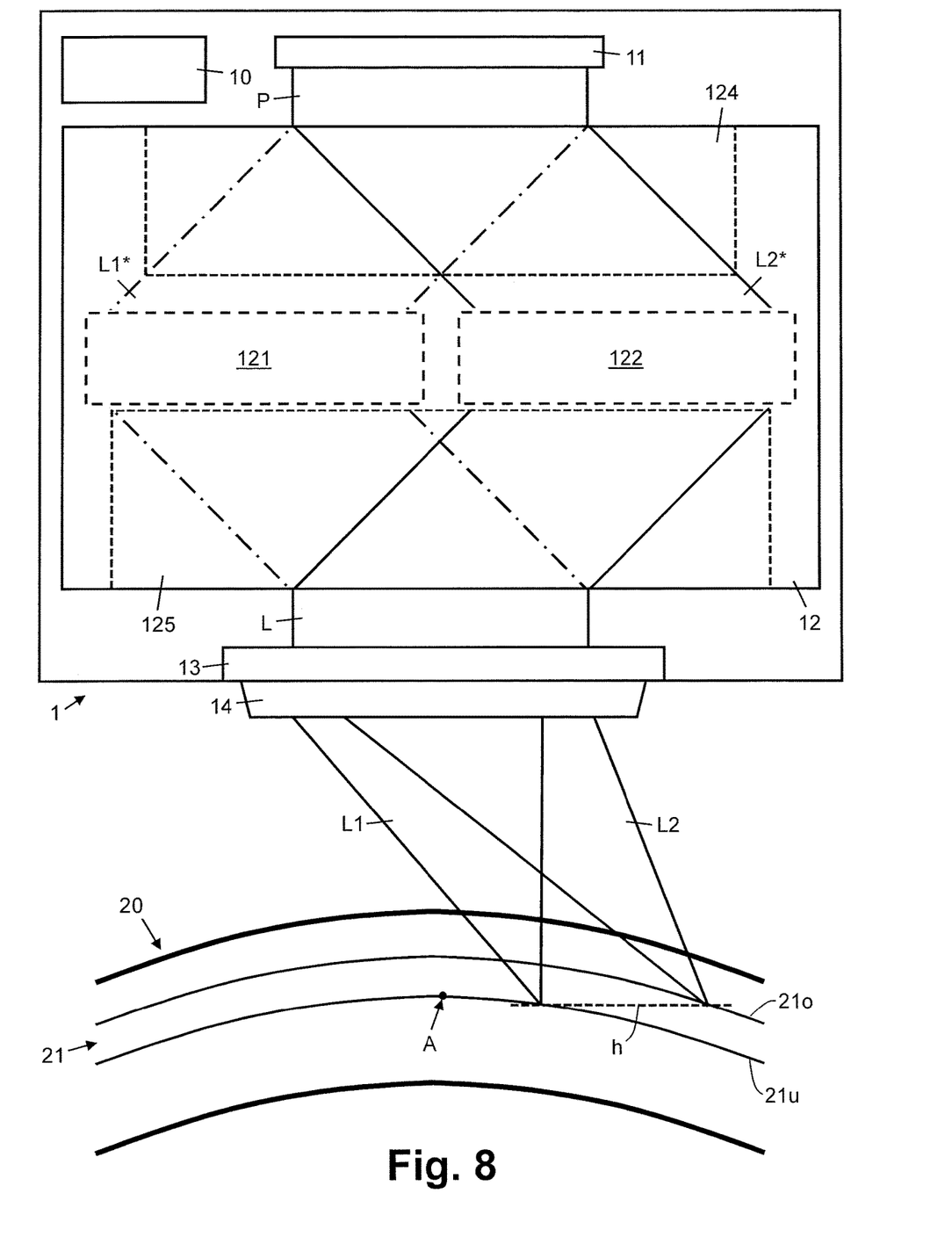
FIG. 8: shows a block diagram of an ophthalmological device for processing eye tissue by means of a pulsed laser beam, which ophthalmological device comprises a beam splitter and a beam combiner for generating a processing laser beam having two beam parts, which are formed by two beam bundles of the pulsed laser beam, said beam bundles proceeding with an angle between their beam axes and are directed in a focused manner onto different outer surfaces of a lenticule to be cut in the eye tissue, as is illustrated schematically in cross section.

The embodiment variants in accordance with FIGS. 6, 7 and 8 differ from those in FIGS. 4 and 5 by virtue of a differently configured beam splitting system 12 and correspondingly adapted control by the circuit 10. The beam splitting system 12 in the embodiment variant in accordance with FIGS. 6, 7 and 8 comprises, like the variant in FIG. 5, a beam splitter 124 and one or two divergence modulators 121, 122, via which the beam splitter 124 feeds the beam bundles L1* and L2* to the beam combiner 125. In contrast to the embodiment variant in FIG. 5, however, the beam combiner 125 is not embodied as a beam cross section combiner 123, but rather as a beam combiner configured to combine the beam bundles L1* and L2* of the pulsed laser beam P, which beam bundles are fed by the beam splitter 124 directly or via the divergence modulator 121, 122, to give the processing laser beam L. Depending on the embodiment variant, the two beam bundles L1*, L2* are combined to give beam parts L1, L2 with a common beam axis (FIGS. 6 and 10) or with an angle between a beam axis of the first beam bundle L1* and a beam axis of the second beam bundle L2* (FIGS. 7, 8 and 11) with respect to the processing laser beam L. By combining the two beam bundles L1*, L2* to give beam parts L1, L2 with an angle between their beam axes (FIGS. 7 and 8), shading and attendant influencing of the two generated foci of the beam parts L1, L2 are avoided without the laser pulses (as in the variant according to FIG. 6) having to be alternately switched to the two beam bundles L1*, L2* for this purpose. In order to set the focus depth overall, the ophthalmological device 1 in these embodiment variants comprises, in addition or as an alternative to the displaceable or settable focus optical unit 14, a zoom system for setting the focus depth on one or both of the beam paths L1*, L2*, said zoom system being arranged upstream or downstream of the one or the two divergence modulators 121, 122. Depending on focusing range and/or technical implementation, in the case of two divergence modulators it is also possible to entirely dispense with a setting of the focusing optical unit and/or zoom systems.

Figure 10:
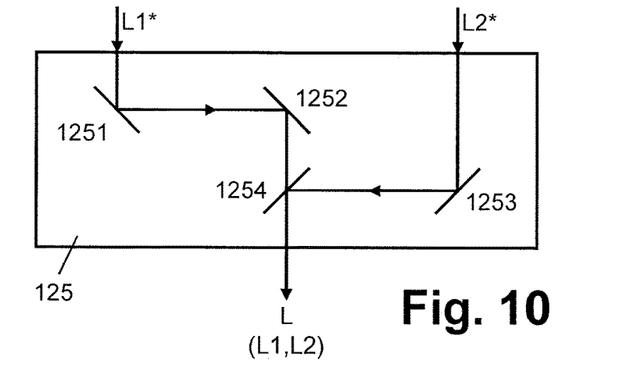
FIG. 10: shows a block diagram of a beam combiner having optical elements for coaxially combining two beam bundles to give a processing laser beam.
Figure 10A:
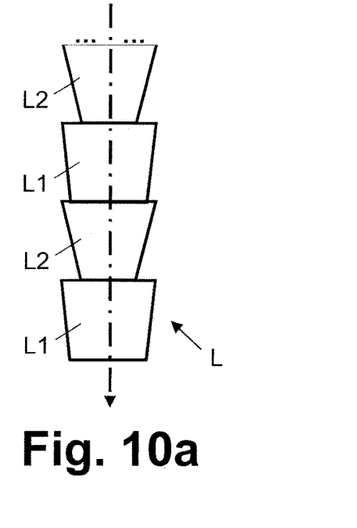
FIG. 10a: schematically illustrates in cross section a processing laser beam having two beam parts, which were generated from two coaxially combined beam bundles having a different divergence.

FIG. 10 illustrates an embodiment variant of the beam combiner 125 having deflection mirrors 1251 and 1252 for coupling in the beam bundle L1* onto the beam path or the beam axis of the processing laser beam L. The beam combiner 125 comprises a further deflection mirror 1253 and a semitransparent mirror 1254 for coaxially coupling in the beam bundle L2* onto the beam path or the beam axis of the processing laser beam L. The person skilled in the art will understand that the two beam bundles L1* and L2* can also be combined via a beam splitter cube. The two beam bundles L1* and L2* proceed coaxially as beam parts L1 and L2 on the beam axis of the processing laser beam L, in each case alternately with a laser pulse from the first beam bundle L1* having a first divergence and a laser pulse from the second beam bundle L2* having a second divergence, as is illustrated schematically in FIG. 10a and as was described above with reference to FIG. 6.

Figure 11:
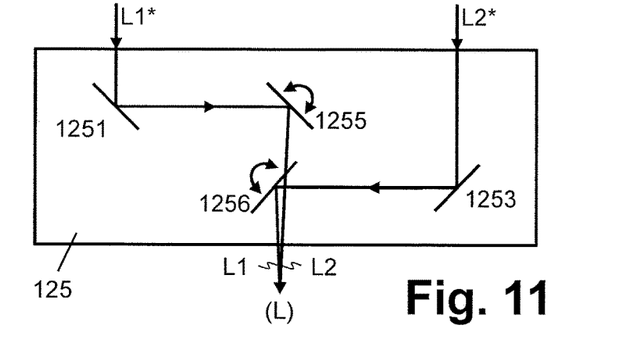
FIG. 11: shows a block diagram of a beam combiner having optical elements for combining two beam bundles to give a processing laser beam with an angle between the beam axes of the beam bundles.
Figure 11A:
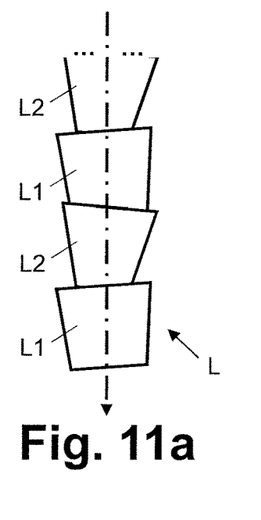
FIG. 11a: schematically illustrates in cross section a processing laser beam having two beam parts, which were generated from two beam bundles having an angle between their beam axes and a different divergence.
Figure 12:
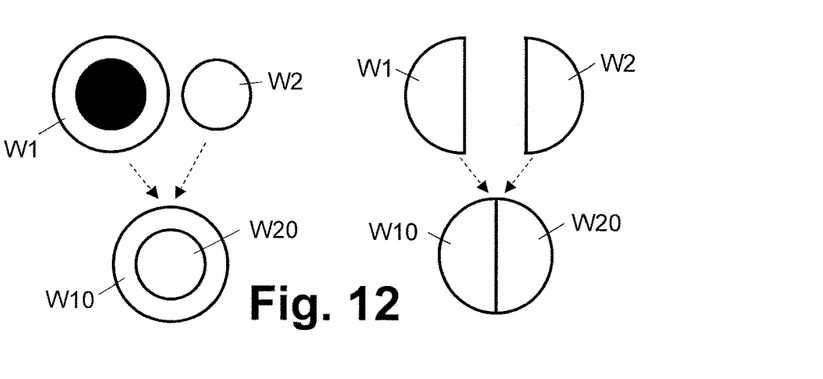
FIG. 12: illustrates examples of non-overlapping beam cross sections of the pulsed laser beam, which do not overlap; on the left beam cross sections arranged concentrically, on the right, beam cross sections arranged alongside one another.

The embodiment variant in accordance with FIG. 11 differs from that in FIG. 10 in that the beam combiner 125 comprises a mirror 1255 and a semitransparent mirror 1256 for coupling in the beam bundles L1*, L2* onto the beam path of the processing laser beam L, at least one of which mirrors is configured in rotatable fashion in such a way that the beam bundles L1* and L2* can be coupled into the beam path of the processing laser beam L with an angle with respect to the beam axis of the processing laser beam L or between the beam axes of the beam bundles L1*, L2*, as was described above with reference to FIGS. 7 and 8. The processing laser beam L generated comprises beam parts L1, L2 proceeding in different directions. In the embodiment variant in accordance with FIG. 7, the successive beam parts L1, L2 additionally differ in their divergence as well. In the embodiment variant in accordance with FIG. 8, the successive beam parts L1, L2 have the same divergence, as described in greater detail below. In a variant in which the beam combining with different beam directions of the beam parts L1, L2 is combined with the beam splitting with alternating pulse switching to the first and respectively second beam bundles L1*, L2*, the processing laser beam L has beam parts L1, L2 proceeding in different directions, in each case alternately with a laser pulse from the first beam bundle L1* having a first beam axis direction and a laser pulse from the second beam bundle L2* having a second beam axis direction, which is different therefrom, as is illustrated schematically in FIG. 11a.

The scanner system 13 directs the processing laser beam L with regard to the x/y positioning for processing the eye tissue 20. For each x/y processing point determined by the scanner system 13 in accordance with a defined scanning pattern, the circuit 10 controls the divergence modulation of the divergence modulators 121, 122, such that a focused processing of the eye tissue 20 on the lower outer surface 21u is effected by means of a laser pulse of the beam part L1 and a focused processing of the eye tissue 20 on the upper outer surface 210 of the lenticule is effected by means of a laser pulse of the beam part L2, without a change in the focusing or focusing optical unit 14 being or having to be carried out for this purpose (apart from by the divergence modulators 121, 122).

In the embodiment variant in accordance with FIG. 8, the beam parts L1, L2 are generated without divergence modulation by the divergence modulators 121, 122, that is to say substantially without a different divergence, and are focused vertically (in the z-direction) with the same depth onto the same horizontal processing plane h, but on account of the angle between the beam axes of the beam bundles L1*, L2* or respectively beam parts L1, L2 are not focused onto the same outer surfaces, but rather with the first beam bundle L1* or respectively beam part L1 onto the lower outer surface 21u and with the second beam bundle L2* or respectively beam part L2 onto the upper outer surface 210 of the lenticule 21 to be cut. By adjusting the processing depth of the processing plane h by means of the focusing optical unit 14 and adjusting the angle between the beam axes of the beam bundles L1*, L2* or respectively beam parts L1, L2 by means of the optical beam combiner of the beam combiner 125 in accordance with FIG. 11, the foci of the beam parts L1, L2 of the processing beam can be tracked to the course of the lower outer surface 21u and the upper outer surface 210 and the lenticule 21 can be cut by deflection of the processing beam by means of the scanner system 13 in accordance with predefined scanning patterns. In this case, the beam bundle L1* or respectively the beam part L1 is stopped if the processing depth of the processing plane h lies above the apex A of the lower outer surface 21u, i.e. if the beam bundle L1* or respectively the beam part L1 reaches the apex, and the beam bundle L2* or respectively the beam part L2 is guided further solely over that region of the upper outer surface 210 which lies above the apex A of the lower outer surface 21u in the z-direction.

Finally, it shall be emphasized that the embodiment variant in accordance with FIG. 7 has the advantage of a particularly simple design. The beam splitting system 12 comprises a beam splitter 124 configured to split the pulsed laser beam P into the first beam bundle L1* for the first beam part L1 and into the second beam bundle L2* for the second beam part L2; a divergence modulator 121 (or 122), configured to modulate the divergence of the first beam part L1 (or of the second beam part L2), such that the two beam parts L1, L2 have a different divergence, in such a way that the first beam part L1 is focused by the focusing optical unit 14 onto the first outer surface 21u and the second beam part L2 onto the second outer surface 210 of the lenticule 21; and a beam combiner 125 configured to combine the first beam bundle L1* and the second beam bundle L2* with an angle between the beam axes of the two beam bundles L1*, L2* to form the processing laser beam L, such that the two beam parts L1, L2 are focused with a different angle of incidence onto the first outer surface 21u and the second outer surface 210 of the lenticule 21. As a result of the different angle of incidence, shading and attendant influencing of the two generated foci of the beam parts L1, L2 are avoided.

The invention claimed is:

1. An Ophthalmological device for cutting a lenticule inside corneal eye tissue, comprising a laser source configured to generate a pulsed laser beam; a focusing optical unit configured to focus a processing laser beam into the corneal eye tissue, and a scanner system configured to direct the processing laser beam into the corneal eye tissue in accordance with predefined scanning patterns;

wherein the ophthalmological device further comprises a beam splitting system disposed upstream of the scanner system and configured to generate the processing laser beam from the pulsed laser beam in such a way that the processing laser beam comprises a first beam part and a second beam part, wherein the first beam part is focused by the focusing optical unit onto a first outer surface of the lenticule to be cut inside the corneal eye tissue, the first outer surface of the lenticule facing away from an external surface of the cornea, and the second beam part is focused onto a different, second outer surface of the lenticule to be cut inside the corneal eye tissue, the second outer surface of the lenticule facing the external surface of the cornea, and, in the course of directing the processing laser beam into the corneal eye tissue by means of the scanner system, the first outer surface is cut inside the corneal eye tissue by the first beam part and the second outer surface is cut inside the corneal eye tissue by the second beam part.

2. The ophthalmological device according to claim 1, wherein the beam splitting system comprises a divergence modulator disposed upstream of the scanner system and configured to modulate a divergence of the first beam part or of the second beam part, such that the first beam part and the second beam part have a different divergence, in such a way that the first beam part is focused onto the first outer surface by the focusing optical unit and the second beam part is focused onto the second outer surface.

3. The ophthalmological device according to claim 1, wherein the beam splitting system comprises a first divergence modulator configured to generate the first beam part with a first divergence; and the beam splitting system comprises a second divergence modulator configured to generate the second beam part with a second divergence, which is different from the first divergence.

4. The ophthalmological device according to claim 3, wherein the focusing optical unit is configured to focus the processing laser beam in the corneal eye tissue onto a set cutting position, the first divergence modulator is configured to generate the first beam part with the first divergence in such a way that the first beam part is focused in the corneal eye tissue relative to the set cutting position onto the first outer surface by the focusing optical unit, and the second divergence modulator is configured to generate the second beam part with the second divergence in such a way that the second beam part is focused in the corneal eye tissue relative to the set cutting position onto the second outer surface by the focusing optical unit.

5. The ophthalmological device according to claim 1, wherein the beam splitting system is configured to split the pulsed laser beam into a first beam bundle and into a second beam bundle.

6. The ophthalmological device according to claim 5, wherein the beam splitting system is configured to feed a first pulse of the pulsed laser beam to the first beam bundle, and to feed a second pulse of the pulsed laser beam, said second pulse directly succeeding the first pulse, to the second beam bundle.

7. The ophthalmological device according to claim 6, wherein the beam splitting system comprises an optical modulator, which is coupled to the laser source in a synchronized manner and is configured to feed the first pulse of the pulsed laser beam to the first beam bundle, and to feed the second pulse of the pulsed laser beam to the second beam bundle.

8. The ophthalmological device according to claim 6, wherein the beam splitting system comprises an optical beam splitter configured to split the pulsed laser beam into the first beam bundle and into the second beam bundle, the beam splitting system comprises a first optical modulator, which is arranged in the first beam bundle in a manner coupled to the laser source in a synchronized manner and is configured to mask out the second pulse of the pulsed laser beam in the first beam bundle, and the beam splitting system comprises a second optical modulator, which is arranged in the second beam bundle in a manner coupled to the laser source in a synchronized manner and is configured to mask out the first pulse of the pulsed laser beam in the second beam bundle.

9. The ophthalmological device according to claim 5, wherein the beam splitting system comprises a beam combiner configured to combine the first beam bundle and the second beam bundle to form the processing laser beam.

10. The ophthalmological device according to claim 9, wherein the beam combiner is configured to combine the first beam bundle and the second beam bundle to form the processing laser beam with an angle between a beam axis of the first beam bundle and a beam axis of the second beam bundle.

11. The ophthalmological device according to claim 9, wherein the beam combiner comprises a beam cross section combiner configured to feed a first cross-sectional region of the first beam bundle to a first cross-sectional region of the processing laser beam, and to feed a second cross-sectional region of the second beam bundle to a second cross-sectional region of the processing laser beam, wherein the first cross-sectional region of the processing laser beam and the second cross-sectional region of the processing laser beam do not overlap.

12. The ophthalmological device according to claim 1, wherein the beam splitting system comprises a beam cross section splitter configured to feed a first cross-sectional region of the pulsed laser beam to the first beam part, and to feed a second cross-sectional region of the pulsed laser beam to the second beam part, wherein the first cross section region and the second cross-sectional region do not overlap.

13. The ophthalmological device according to claim 12, wherein the beam splitting system comprises a beam cross section combiner configured to feed the first cross-sectional region of the pulsed laser beam to a first cross-sectional region of the processing laser beam, and to feed the second cross-sectional region of the pulsed laser beam to a second cross-sectional region of the processing laser beam, wherein the first cross-sectional region of the processing laser beam and the second cross-sectional region of the processing laser beam do not overlap.

14. The ophthalmological device according to claim 1, wherein the scanner system is configured to direct the processing laser beam into the corneal eye tissue in accordance with a predefined cutting line scanning pattern, wherein the first beam part generates a first cutting line on the first outer surface of the lenticule and the second beam part generates a second cutting line on the second outer surface of the lenticule.

15. The ophthalmological device according to claim 14, wherein the scanner system comprises a first scanner module configured to guide the processing laser beam in accordance with a first component of the predefined cutting line scanning pattern in an advance direction along a processing line, and the scanner system comprises a second scanner module configured to direct the processing laser beam in accordance with a second component of the predefined cutting line scanning pattern, said second component being superimposed on the first component, along a scanning line running transversely with respect to the processing line, at a significantly higher scanning speed in comparison with the scanning speed of the first scanner module in the advance direction, wherein the first beam part generates a first cutting line having the first component and the superimposed second component on the first outer surface of the lenticule and the second beam part generates a second cutting line having the first component and the superimposed second component on the second outer surface of the lenticule.

16. The ophthalmological device according to claim 1, wherein the beam splitting system is configured to generate the first beam part and the second beam part in such a way that the first beam part is focused by the focusing optical unit onto the first outer surface, which is further away from the focusing optical unit than the second outer surface, onto which the second beam part is focused by the focusing optical unit.

17. An apparatus comprising:
   a laser source configured to generate a pulsed laser beam;
   a beam splitting system configured to generate a processing laser beam from the pulsed laser beam in such a way that the processing laser beam comprises a first beam part and a second beam part;
   a scanner system, disposed downstream of the beam splitting system, configured to direct the processing laser beam into corneal eye tissue in accordance with predefined scanning patterns; and
   a focusing optical unit configured to focus the processing laser beam into the corneal eye tissue, wherein the first beam part is focused by the focusing optical unit onto a first outer surface of a lenticule to be cut inside the corneal eye tissue, the first outer surface of the lenticule facing away from an external surface of the cornea, and the second beam part is focused onto a different, second outer surface of the lenticule to be cut inside the corneal eye tissue, the second outer surface of the lenticule facing the external surface of the cornea.

18. The apparatus of claim 17, wherein the beam splitting system comprises a divergence modulator, disposed upstream of the scanner system, configured to modulate a divergence of the first beam part or of the second beam part, such that the first beam part and the second beam part have a different divergence, in such a way that the first beam part is focused onto a first outer surface by the focusing optical unit and the second beam part is focused onto a second outer surface.

19. An apparatus comprising:
a laser source configured to generate a pulsed laser beam;
a beam splitting system configured to generate a processing laser beam from the pulsed laser beam in such a way that the processing laser beam comprises a first beam part and a second beam part;
a scanner system configured to direct the processing laser beam into corneal eye tissue in accordance with predefined scanning patterns; and
a focusing optical unit configured to focus the processing laser beam into the corneal eye tissue,
wherein the first beam part is focused by the focusing optical unit onto a first outer surface of a lenticule to be cut inside the corneal eye tissue, the first outer surface of the lenticule facing away from an external surface of the cornea, and the second beam part is focused onto a different, second outer surface of the lenticule to be cut inside the corneal eye tissue, the second outer surface of the lenticule facing the external surface of the cornea, and, in the course of directing the processing laser beam into the corneal eye tissue by means of the scanner system, the first outer surface is processed by the first beam part and the second outer surface is processed by the second beam part.

20. The apparatus of claim 19, wherein the beam splitting system comprises:
a first divergence modulator configured to generate the first beam part with a first divergence; and
a second divergence modulator configured to generate the second beam part with a second divergence, which is different from the first divergence.

* * * * *